US00PP32349P3

(12) United States Plant Patent
Bell et al.

(10) Patent No.: US PP32,349 P3
(45) Date of Patent: Oct. 20, 2020

(54) BLUEBERRY PLANT NAMED 'MG09768-05-002'

(50) Latin Name: ***Vaccinium* hybrid**
Varietal Denomination: MG09768-05-002

(71) Applicant: Moondarra Genetics Pty Ltd, Moondarra, Victoria (AU)

(72) Inventors: Ridley Bell, Lindendale (AU); Joel Deveson, Newborough (AU)

(73) Assignee: Moondarra Genetics PTY LTD, Moondarra (AU)

( * ) Notice: Subject to any disclaimer, the term of this patent is extended or adjusted under 35 U.S.C. 154(b) by 0 days.

(21) Appl. No.: 16/501,661

(22) Filed: May 20, 2019

(65) Prior Publication Data

US 2019/0364709 P1 Nov. 28, 2019

Related U.S. Application Data

(60) Provisional application No. 62/762,825, filed on May 22, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Plant & Planet Law Firm

(57) ABSTRACT

The new blueberry plant variety 'MG09768-05-002' is provided. 'MG09768-05-002' is a commercial variety intended for the fresh fruit market. The variety is produced from a cross of 'Magnolia' and 'Caroline', which can be distinguished by its outstanding features.

2 Drawing Sheets

Latin name of the genus and species:
Genus—*Vaccinium.*
Species—hybrid.
Variety denomination: The new blueberry plant claimed is of the variety denominated 'MG09768-05-002'.

BACKGROUND OF THE INVENTION

The proposed new *Vaccinium* variety 'MG09768-05-002' was selected as a seedling from a controlled pollination involving southern and northern highbush varieties 'Magnolia' (seed parent) (not patented) and 'Caroline' (pollen parent) (not patented) respectively. The cross was made in 2009 in Moondarra, Victoria, Australia and the variety was first selected in 2016 in Moondarra, Victoria, Australia. This new cultivar has been asexually propagated through cuttings since 2016 and grown in replicated field trials from 2017 in Moondarra, Victoria, Australia.

The fruit of 'MG09768-05-002' is large and crunchy with excellent flavor, good bloom and a small dry scar. The bush is very vigorous with an upright growth habit.

SUMMARY OF THE INVENTION

As mentioned above, the proposed new variety is a result of the cross of 'Magnolia' and 'Caroline'.

The seed parent 'Magnolia' was selected in Poplaville, Miss. in 1982 in respect to its early fruit ripening, low chill requirement, vigorous growth, medium sized/firm fruit with good flavor.

The pollen parent was produced from open pollinated 'Lateblue' (not patented) seeds sent to the Knoxfield Horticultural Research Institute in Victoria, Australia in 1976, and was selected based on its medium timing of fruit ripening, strong aromatic flavor, medium firmness and moderate bush vigor.

The proposed new variety 'MG09768-05-002' is a resulting selection from seedlings produced out a controlled pollination event between 'Magnolia' and 'Caroline' in the breeding program at Moondarra, Victoria, Australia in 2009.

Asexual reproduction of the proposed new variety 'MG09768-05-002' via softwood cuttings has occurred since 2016 at Moondarra, Victoria, Australia. This has demonstrated that the new variety is uniform, stable and true to type over successive generations of asexual propagation in respect to the characteristics aforementioned.

The proposed new cultivar 'MG09768-05-002' was selected as a single plant in a population of seedlings resulting from a cross between the southern highbush variety 'Magnolia' and northern highbush variety 'Caroline' being selected in 2016 at Moondarra, Victoria, Australia. Its selection was based on the criteria of strong bush vigor, mid-season fruit ripening, large/crunchy berry with an excellent flavor and good bloom. The selection has been evaluated in field trials at Moondarra, Victoria, Australia since 2017.

The following characteristics of the proposed new variety have been observed and used to distinguish 'MG09768-05-002' as a distinct cultivar of *Vaccinium* hybrid:

Mid-season fruit ripening.
Strong plant vigor.
Upright/whippy growth habit.
Large berry size.
Crunchy berry texture.
Small dry picking scar.

The proposed new variety 'MG09768-05-002' is uniform, stable and true to type over successive generations of asexual propagation through softwood cuttings in respect to the characteristics aforementioned.

The new cultivar 'MG09768-05-002' differs from the seed parent 'Magnolia' previously described in terms of its mid-season fruit ripening, higher chill requirement, larger berry size and crunchy berry texture.

'MG09768-05-002' differs from pollen parent 'Caroline' in respect to a larger berry size, crunchy berry texture and strong bush vigor.

BRIEF DESCRIPTION OF THE DRAWINGS

The accompanying photographic illustration shows typical specimens in full color of the foliage and fruit of the new variety 'MG09768-05-002'. 'MG09768-05-002' has been labeled NB-5-2 in the photographs. The colors are as nearly true as is reasonably possible in a color representation of this type.

Figure 1:
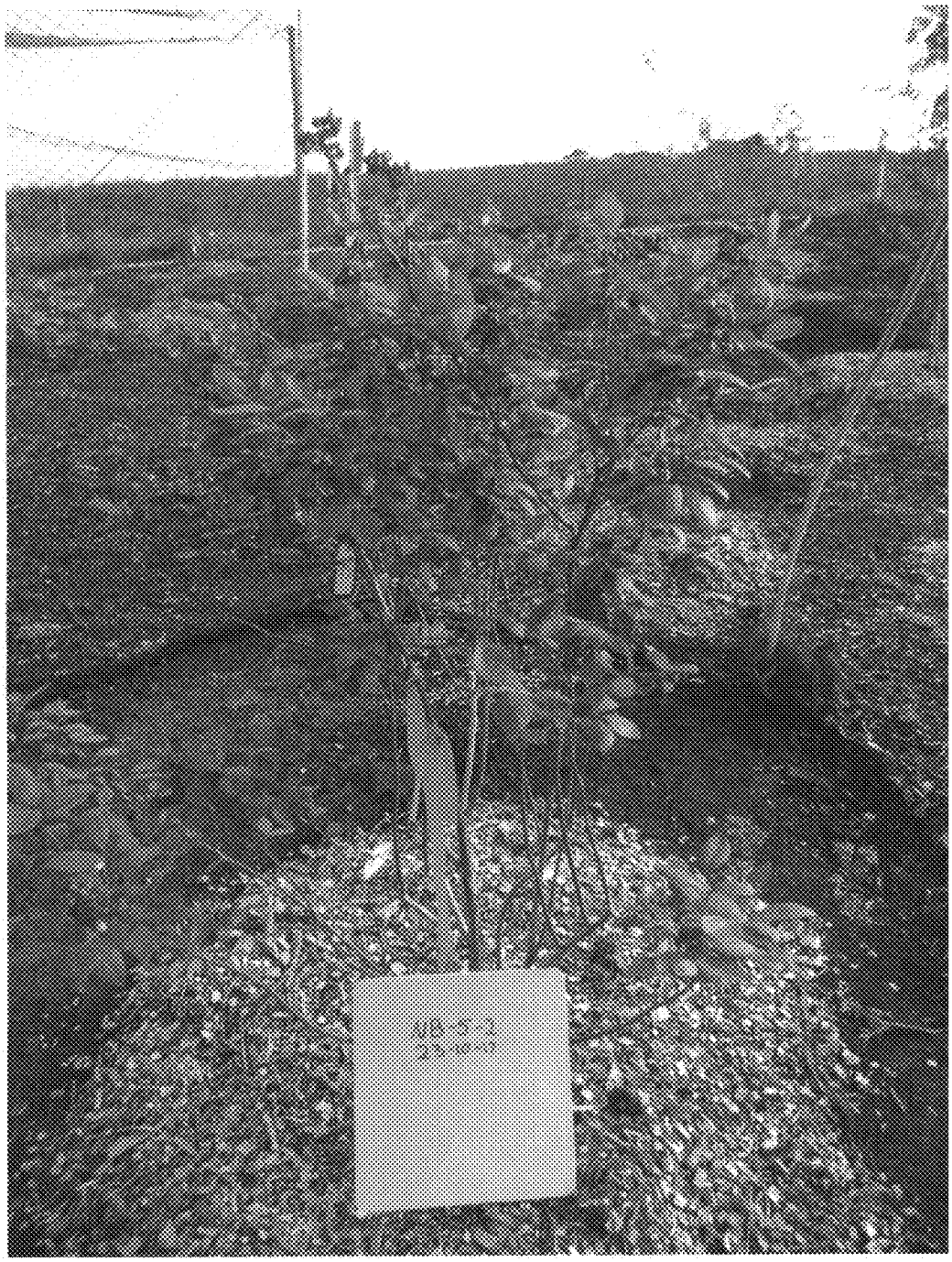
FIG. 1 is a photograph of the new variety 'MG09768-05-002', demonstrating the plant's upright/whippy growth habit at age 6-7 years.
Figure 2:
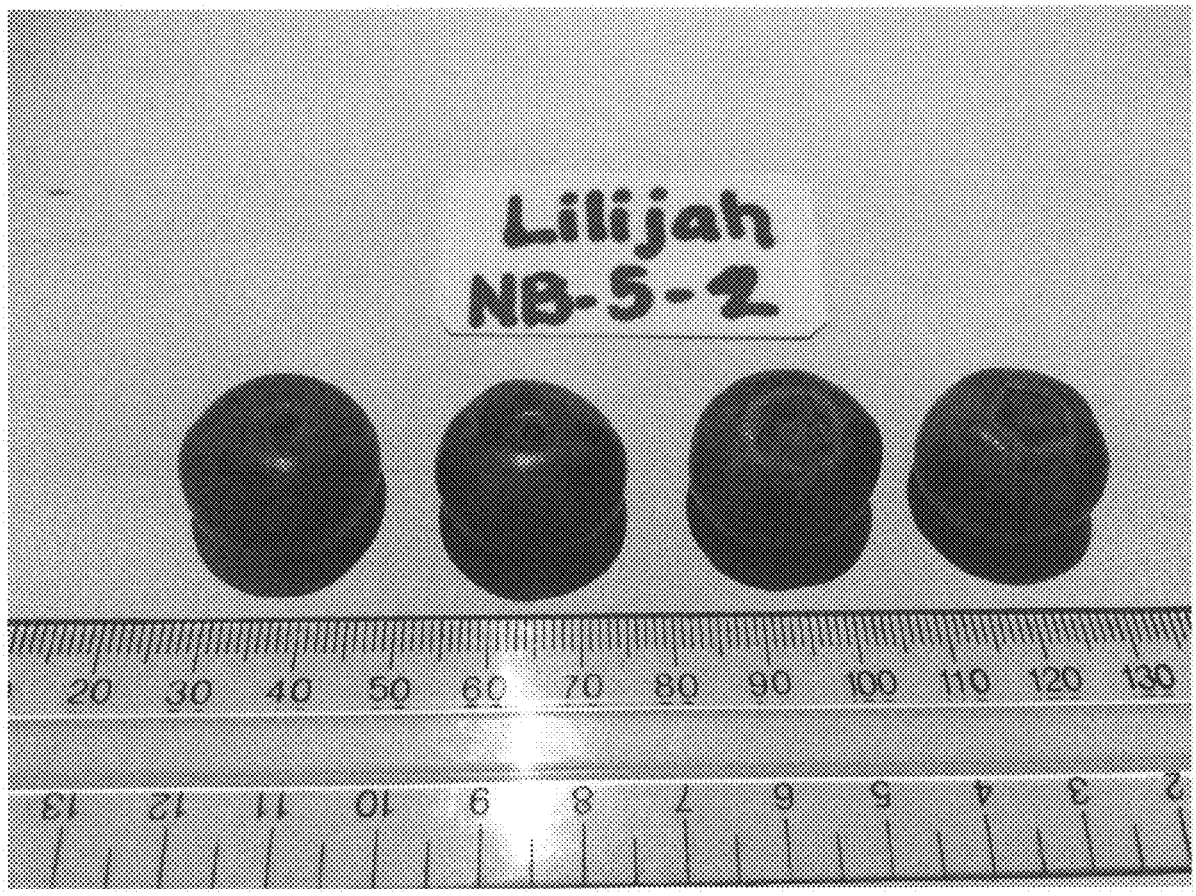
FIG. 2 is a photograph of the fruit of the new variety 'MG09768-05-002' at age 6-7 years.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'MG09768-05-002'. The data which defines these characteristics was collected from asexual reproductions of the original selection. Dimensions, sizes, colors, and other characteristics are approximations and averages set forth as accurately as possible. The plant history was taken on plants approximately 3 years of age, and the descriptions relate to plants grown in the field in Moondarra, Victoria, Australia. Descriptions of fruit characteristics were made on fruit grown in Moondarra, Victoria, Australia. Color designations are from Pantone Color Bridge plus.

Classification:

*a. Family.*—Ericaceae.
*b. Genus.*—*Vaccinium.*
*c. Species.*—hybrid.
*d. Common name.*—Blueberry.

Parentage: Female Parent—'Magnolia' (not patented). Male Parent—'Caroline' (not patented).

Market class: A fruiting plant intended for the fresh fruit market.

PLANT

General:

*a. Parentage.*—'Magnolia' x 'Caroline'.
*b. Plant height.*—0.8-1 m.
*c. Plant width.*—0.5-0.6 m.
*d. Growth habit.*—Upright/whippy.
*e. Growth (vigor).*—Strong-very strong.
*f. Productivity.*—Medium to high (~6.6 kg/plant).
*g. Cold hardiness.*—Not tested.
*h. Cold tolerance.*—Not tested.
*i. Chilling requirement.*—Not tested.
*j. Tolerance to disease.*—Not tested.
*k. Leafing.*—Strong to very strong.
*l. Twigginess.*—Moderate.

STEM

General:

*a. Suckering tendency.*—4-5/plant.
*b. Mature cane color.*—199B/165BC.
*c. Mature cane length.*—0.7-0.75 m.
*d. Mature cane width.*—~1 cm.
*e. Bark texture.*—Medium roughness.
*f. Surface texture of new wood.*—Smooth.
*g. Internode length on strong, new shoots.*—~18 mm.
*h. Fruiting wood.*—Up to 18 cm in length.

FOLIAGE

General:

*a. Time of beginning of leaf bud burst.*—Mid-late September.
*b. Leaf color (top side).*—148A/147A.
*c. Leaf color (under side).*—145B.
*d. Leaf arrangement.*—Alternate.
*e. Leaf shape.*—Elliptic.
*f. Leaf margins.*—Entire.
*g. Undulation of margin.*—Weak.
*h. Leaf venation.*—Reticulate.
*i. Leaf apices.*—Acute.
*j. Leaf bases.*—Obtuse.
*k. Leaf length.*—58-64 mm.
*l. Leaf width.*—26-28 mm.
*m. Leaf length/width ratio.*—Medium; about 1:0.44.
*n. Leaf nectarines.*—Absent.
*o. Pubescence of upper side.*—Absent.
*p. Pubescence of lower side.*—Absent.
*q. Cross sectional profile.*—Flat.
*r. Longitudinal profile.*—Straight.
*s. Attitude.*—Semi-upright.

Petioles:

*a. Length.*—~5 mm.
*b. Width.*—1.5-2 mm.
*c. Color.*—Yellow-Green 144D.

FLOWERS

General:

*a. Time of beginning of flowering.*—25$^{th}$ September.
*b. Time of* 50% anthesis.—8$^{th}$ October.
*c. Flower shape.*—Urceolate.
*d. Flower bud density.*—Moderate to high (8 buds/lateral).
*e. Flower fragrance.*—Weak; sweet smell.

Corolla:

*a. Length.*—~9 mm.
*b. Width.*—7-8 mm.
*c. Aperture width.*—~4 mm.
*d. Anthocyanin coloration of corolla.*—Absent.
*e. Corolla ridges.*—Present.
*f. Protrusion of stigma.*—Absent.

Inflorescence:

*a. Length.*—25-30 mm.
*b. Diameter.*—28-32 mm.
*c. Length of peduncle.*—4-5 mm.
*d. Surface texture of peduncle.*—Smooth.
*e. Color of peduncle.*—145B/144C/D.
*f. Length of pedicel.*—8-10 mm.
*g. Surface texture of pedicel.*—Smooth.

*h. Color of pedicel.*—140B/144C/D.
*i. Number of flowers per cluster.*—6-7.
*j. Flower cluster density.*—Moderate.

Calyx (with sepals):
*a. Diameter.*—7-8 mm.
*b. Color (sepals).*—145B/144A.

Stamen:
*a. Length.*—6-7 mm.
*b. Number per flower.*—10-12.
*c. Filament color.*—142C/145C.

Style:
*a. Length.*—8-9 mm.
*b. Color.*—145B/140B.

Pistil:
*a. Length.*—10-12 mm.
*b. Ovary color (exterior).*—149C/144A.

Anther:
*a. Length.*—3-4 mm.
*b. Number.*—10-12.
*Color.*—167A/164C.

Pollen:
*a. Self-compatibility.*—Good (~80%).

FRUIT

General:
*a. Time of fruit ripening.*—Late December/early January at Moondarra, Victoria, Australia.
*b. Time of 50% maturity.*—Early to mid-January.
*c. Fruit development period.*—Approximately 80-90 days.
*d. Cluster density.*—~23 berries per cluster.
*e. Unripe fruit color.*—142C.
*f. Ripe berry color.*—203C/103A.
*g. Berry surface wax abundance.*—Moderate-strong.
*h. Berry flesh color.*—149C/D.
*i. Berry weight.*—2.84 g.
*j. Berry height from calyx to scar.*—12-13 mm.
*k. Berry diameter.*—20-23 mm.
*l. Berry shape.*—Oblate.
*m. Fruit stem scar.*—Small/dry.
*n. Sweetness when ripe.*—Medium to high.
*o. Firmness when ripe.*—Firm.
*p. Acidity when ripe.*—Medium to high.
*q. Storage quality.*—Very good.
*r. Suitability for mechanical harvesting.*—Not suitable.
*s. Self-fruitfulness.*—Yes.
*t. Uses.*—Fresh fruit.

SEED

General:
*a. Seed abundance in fruit.*—Moderate.
*b. Seed length.*—1-2 mm.

COMPARISON BETWEEN COMMERCIAL CULTIVARS

| Organ | Context | 'MG09768-05-02' | 'Brigitta' (not patented) |
|---|---|---|---|
| Plant | Vigor | Strong | Medium |
| Plant | Growth habit | Upright to semi-upright | Upright |
| One-year-old shoot | Color | Greenish red | Green |
| One-year-old shoot | Length of internode | Medium | Medium |
| Leaf | Length | Medium | Long |
| Leaf | Width | Medium | Broad |
| Leaf | Shape | Elliptic | Elliptic |
| Leaf | Color of upper side | Green | Green |
| Leaf | Intensity of green color on upper side (varieties with green leaf color only) | Light to medium | Medium |
| Leaf | Margin | Entire | Serrate |
| Flower bud | Anthocyanin coloration | Weak to medium | Medium-strong |
| Flower | Shape of corolla | Urceolate | Urceolate |
| Flower | Size of corolla tube | Medium | Medium |
| Flower | Anthocyanin coloration of corolla tube | Absent or very weak | Absent or very weak |
| Flower | Ridges on corolla tube | Present | Present |
| Fruit cluster | Density | Sparse | Medium-dense |
| Unripe fruit | Intensity of green color | Light | Light |
| Fruit | Size | Large | Medium |
| Fruit | Shape in longitudinal section | Oblate | Oblate |
| Fruit | Attitude of sepals | Erect | Erect |
| Fruit | Diameter of calyx basin | Small to medium | Small-medium |
| Fruit | Depth of calyx basin | Shallow to medium | Deep |
| Fruit | Intensity of bloom | Medium to strong | Medium |
| Fruit | Color of skin | Dark blue | Dark blue |
| Fruit | Firmness | Soft to medium | Medium |
| Fruit | Sweetness | Medium to high | Low-medium |
| Fruit | Acidity | Medium to high | Low-medium |
| Time of | Vegetative bud burst | Early to medium | Medium |
| Time of | Beginning of flowering | Medium | Medium |
| Time of | Beginning of fruit ripening | Medium | Medium |

-continued

COMPARISON BETWEEN COMMERCIAL CULTIVARS

| Organ | Context | 'Legacy' (not patented) |
|---|---|---|
| Plant | Vigor | Medium to strong |
| Plant | Growth habit | Upright to semi-upright |
| One-year-old shoot | Color | Reddish yellow |
| One-year-old shoot | Length of internode | Short to medium |
| Leaf | Length | Medium |
| Leaf | Width | Medium |
| Leaf | Shape | Elliptic |
| Leaf | Color of upper side | Green |
| Leaf | Intensity of green color on upper side (varieties with green leaf color only) | Medium to dark |
| Leaf | Margin | Entire |
| Flower bud | Anthocyanin coloration | Weak |
| Flower | Shape of corolla | Urceolate |
| Flower | Size of corolla tube | Medium |
| Flower | Anthocyanin coloration of corolla tube | Absent or very weak |
| Flower | Ridges on corolla tube | Present |
| Fruit cluster | Density | Medium |
| Unripe fruit | Intensity of green color | Light |
| Fruit | Size | Medium |
| Fruit | Shape in longitudinal section | Oblate |

-continued

| COMPARISON BETWEEN COMMERCIAL CULTIVARS | | |
|---|---|---|
| Fruit | Attitude of sepals | Erect to semi-erect |
| Fruit | Diameter of calyx basin | Small |
| Fruit | Depth of calyx basin | Medium to deep |
| Fruit | Intensity of bloom | Medium |
| Fruit | Color of skin | Dark blue |
| Fruit | Firmness | Medium |
| Fruit | Sweetness | Medium |
| Fruit | Acidity | Medium |
| Time of | Vegetative bud burst | Early to medium |
| Time of | Beginning of flowering | Early to medium |

-continued

| COMPARISON BETWEEN COMMERCIAL CULTIVARS | | |
|---|---|---|
| Time of | Beginning of fruit ripening | Medium |

What is claimed is:

1. A new and distinct variety of blueberry plant named 'MG09768-05-002', substantially as illustrated and described herein.

* * * * *